United States Patent [19]

Crutcher

[11] Patent Number: 4,867,967
[45] Date of Patent: Sep. 19, 1989

[54] METHOD FOR THE TREATMENT OF PSEUDOFOLLICULITIS BARBAE

[76] Inventor: Wilbert L. Crutcher, 222 E. Chestnut St., Chicago, Ill. 60611

[21] Appl. No.: 58,182

[22] Filed: Jun. 4, 1987

[51] Int. Cl.$^4$ .................. A61K 7/15; A61K 31/79
[52] U.S. Cl. .................................. 424/73; 424/80; 514/848
[58] Field of Search .............. 424/80, 73; 514/864, 514/848

[56] References Cited

U.S. PATENT DOCUMENTS

| 4,301,145 | 11/1981 | Cestari | 424/80 |
| 4,401,651 | 8/1983 | Knutson | 424/80 |
| 4,463,016 | 7/1984 | Burgess | 514/737 |
| 4,671,957 | 6/1987 | Holtshousen | 424/80 |

FOREIGN PATENT DOCUMENTS 1165244 4/1984 Canada .

Primary Examiner—Joseph L. Schofer
Assistant Examiner—Peter F. Kulkosky

[57] ABSTRACT

A method of treating pseudofolliculitis barbae in humans and the prophylactic treatment thereof which comprises topically applying to the body of a person in need of such treatment povidone-iodine in an amount effective to treat and prevent pseudofolliculitis barbae wherein the povidone-iodine is in combination with a vehicle which facilitates the topical application of said povidone-iodine.

1 Claim, No Drawings

METHOD FOR THE TREATMENT OF PSEUDOFOLLICULITIS BARBAE

BACKGROUND OF THE INVENTION

1. Field of the Invention

The present invention is a method for the treatment of pseudofolliculitis barbae (shaving and razor bumps). More particularly, the present invention is directed to a method of treating pseudofolliculitis barbae in humans and the prophylactic treatment thereof which comprises topically applying to the body of a person suffering from pseudofolliculitis barbae an effective amount of povidone-iodine to treat and prevent pseudofolliculitis barbae wherein said povidone-iodine is in combination with a vehicle which facilitates topical application.

2. Background of the Invention and Description of Prior Art

Many if not most men want a good, clean shave in order to have a smooth face and a well-groomed look. Black men are no exception. Most black men shave in order to have a clean-cut image in their respective careers in the military, business or in the professions. The use of soaps, shaving creams and gels and aftershave lotions and balms are used widely by men as grooming products to obtain and maintain a clean shave and smooth face.

However, some men, and black in particular, have a skin condition that makes obtaining a clean-shaven, smooth face difficult. Particularly, they suffer from pseudofolliculitis barbae. Gary J. Brauner, MAJ., MC, and Kenneth L. Flandermeyer, MAJ., MC, two doctors who conducted important research reported in an article titled "Pseudofolliculitis Barbae. 2. Treatment", International Journal of Dermatology, Vol. 16 pages 520–525, 1977, stated that pseudofolliculitis barbae is a disease affecting essentially only blacks and almost all (83%) of those blacks who shave. Due to the tendency of black hair to form tight coils and spirals and an inherent curvature of the hair follicle, the hair will normally curve back toward the surface of the skin. When the free end of this hair is sharpened by the shaving process, it acts like a hook and penetrates the epidermis, resulting in a foreign body reaction in the dermis. This is subsequently complicated by secondary bacterial infection. The disease commonly affects the anterior neckline and the chin can also involve the maxillary prominence of the cheeks. The axilla and pubis when shaved, can be affected.

Clinically the disease is characterized by papules and papulopustules that, when shaved over, can be very painful and bleed easily. Bacteria plays a role in the process of this disease.

Various forms of treatment and shaving methods have been suggested to solve the problem of pseudofolliculitis barbae. The Russell Student Health Center at the University of Alabama conducted a pseudofolliculitis barbae clinic to help male students. Black males were the patients primarily affected by pseudofolliculitis barbae, but a few white males with coarse, curly hair also had the problem. John G. Galaznik, from the Russel Student Health Center at the University of Alabama commented in an article titled "A Pseudofolliculitis Barbae Clinic for the Black Male Who Has to Shave" Journal of American College Health, Vol. 33, Pages 126–127, December 1984, that the idea treatment is to grow a beard. However, the disadvantage to this treatment is that many campus organizations, some athletic coaches, and all ROTC and military units have regulations against beards. Furthermore, many black males have just enough facial hair to cause problems but not enough hair to grow a presentable beard. Frequently students try to schedule their lives around their shaving, i.e., shaving only once a week before ROTC drills or before games. This is possible in college when students can look unshaven half the time, but in the military, business and professional worlds, this is unrealistic. Galaznik reported: that careful shaving with a razor blade shaver as treatment is most harmful as it cuts at or below the skin line, sharpens the hair to a point, and irritates and cuts existing pseudofolliculitis barbae bumps causing bleeding and further scarring. One company produces a blade razor with a spacer over the blade to prevent it from cutting too close. This may work for some patients; however, most said it still irritated existing bumps and did not stop further bumping.

Electric shavers are used as an alternative by some blacks. In general, it is more difficult to achieve a close shave with this method of hair removal. The electric shaver will not pick up the very coarse, curly hairs lying snugly against the skin surface. These are the ones most likely to cause new bumps. Many black men have found the electric shaver an unsuitable shaving alternative for treating pseudofolliculitis barbae.

Chemical depilatories, as treatment for pseudofolliculitis barbae work for some black men. However, many complain that they are time-consuming to use and are too harsh and irritating on the skin, consequently, frequent usage for maintaining a clean shave is not possible without harming the skin, stated Galaznik.

Other methods for treatment are disclosed by Louis A. Brown, Jr., M.D., in a discussion of pseudofolliculitis barbae titled "Pathogenesis and Treatment of Pseudofolliculitis Barbae", Cutis, Vol. 32, pages 373-375, October 1983. Brown believed that the use of topical or low-dose systemic antibotics could help ameliorate pseudofolliculitis barbae. It has been pointed out that while bacteria are not the initiating factor in pseudofolliculitis barbae, colonization by normal flora may lead to more exuberant inflammation due to secondary infection. Topical antibiotics twice daily (Cleocin T ™ topical solution or A/T/S ™) and/or low-dose systemic antibiotics (tetracycline or erthromycin 250 mg twice a day) may be quite effective in limiting the inflammatory process until such time that the inciting hair can be freed. The disadvantage to this and similar methods of treatment utilizing antibiotics is that prescriptions may be needed and can't be used on a daily basis by black males who can't afford to see a doctor for a prescription. Also these antibiotics may be too strong for some consumers with mild cases of pseudofolliculitis barbae.

Another method that Brown had used with limited success is the use of topical retionic acid. However, use of this as therapy has to be terminated in most cases due to irritation encountered.

Another treatment of pseudofolliculitis barbae mentioned by Brown is the complete removal of hair: epilation. Techniques for accomplishing this range from crude manual plucking to electrolysis, and to surgical undermining followed by follicular destruction. Brown dismisses hair plucking outright since in more cases than not, the complete hair is not removed, but rather the remaining stub proceeds to penetrate the follicular wall leading to exacerbation of the disease.

The methods of electrolysis and surgical removal of hair are too costly for the average black male and can also be quite painful.

It is clear that the prior mentioned methods of treating pseudofolliculitis barbae are not satisfactory solutions for the bulk of black male shavers in our society.

Most black male shavers therefore would find it desirable to have an affordable easy-to-use skin care product that can be used on a daily basis, as a treatment for pseudofolliculitis barbae. A satisfactory skin care method to treat pseudofolliculitis barbae should have superior disinfecting, germ-killing, properties to inhibit the secondary bacterial infection that helps cause pseudofolliculitis barbae. In particular, the composition should have good acceptable tactile properties that exhibit a satisfactory feel when applied to the skin, in addition to antiseptic properties to kill germs and styptic properties to arrest bleeding from razor bumps that have been cut while shaving. This skin care composition should help allow the skin to heal as quickly as possible.

Until now, prior art and commercially available cosmetic formulations have failed to achieve all the aforementioned desired properties. U.S. Pat. No. 4,228,163 describes a combination of benzoyl peroxide and chlorohydroxyquinoline which provides keratolytic and antimicrobial activity to release hairs and prevent infection. U.S. Pat. No. 4,463,016 was issued for 4-chloro 3,5-diloweralkylphenol for treatment of pseudofolliculitis barbae as topical cream. Canadian Pat. No. 1,165,244 describes a lubricating shaving preparation for individuals with pseudofolliculitis barbae containing a cationic quaternary ammonium polymer.

Published data to support the efficacy of these preparations on pseudofolliculitis barbae are not readily available. I have been unable to locate these preparations in stores. Recently, other attempts have been made to help ameliorate the condition of pseudofolliculitis barbae with the introduction of various skin care products as Bump-Off, High Time, Ef-Kay, Bump-Phree. These products are subject to various defects. In general, after discussions with people who have tried these various products, it has been repeatedly stated that none of them are effective in treating and preventing pseudofolliculitis barbae satisfactorily. After personal use of these products I also conclude that none of the above-mentioned products are effective in treating pseudofolliculities barbae in a satisfactory manner. However, I have tried a solution of povidone-iodine to fight pseudofolliculitis barbae and have found that it works.

3. SUMMARY OF THE INVENTION

A methodology for treating pseudofolliculitis barbae in humans and the prophylactic treatment thereof, which comprises topically applying to the human body an effective amount of povidone-iodine, which is an effective broad spectrum anti-microbial, topical anti-infective agent of the formula: $(C_6H_9NO)_n \cdot xI$ 2-Pyrrolidinone, 1-ethenyl-, homopolymer, compd. with iodine; 1-Vinyl-2-pyrrolidinone polymer, compared with iodine. The chemical structure of the foregoing is reflected in the following symbol, taken from The United States Pharmacopeia XXI Revision and the National Formulary, XVI Edition at Page 863:

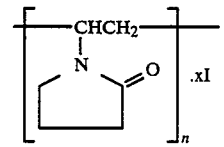

Povidone-Iodine is a complex of Iodine with Povidone. The methodology discussed herein for the treatment of pseudofolliculitis barbae puts povidone-iodine in combination with a vehicle which facilitates the topical application of said povidone-iodine.

Povidone-iodine is an effective broad spectrum antimicrobial agent used in the treatment of both gram negative and gram positive bacteria, fungi, yeast and protozoa. Povidone-iodine preparations are widely used as hand-washes for health care personnel; as surgical scrubs; to prepare skin prior to surgery, injection, or aspiration; to treat minor cuts and abrasions; to treat burns and as a disinfectant for urinary catheters and peritoneal dialysis equipment. Povidone-iodine may be used locally as a vaginal disinfectant in the treatment of trichomoniasis.

4. DETAILED DESCRIPTION OF THE INVENTION

I have discovered that povidone-iodine in combination with an application vehicle, of any type, for a composition of povidone-iodine that can be topically applied and smeared onto the skin, is especially effective in the treatment of pseudofolliculitis barbae and its associated symptoms of inflammation and infection. Povidone-iodine is a powerful anti-infective agent effective in the treatment of bacterial infections in humans. Thus, bacterial infections which are secondary to the underlying folliculitis and are caused by bacteria are among the skin infections contemplated to be treated by the method herein.

The povidone-iodine may be administered to the chin, neck and jowl for the treatment of pseudofolliculitis barbae in the form of, but not limited to, a cream, salve, gel, lotion, balm or sudsing agent cleanser.

Such a cream, salve, gel, lotion, balm or sudsing agent cleanser should, preferably, contain the povidone-iodine complex in concentrations in the range from about 0.05% to about 30.0%, by weight, of the total formulation in which the povidone-iodine complex is in combination with the applying vehicle, to make up a composition for topical application. Such a composition in addition to containing an effective amount of povidone-iodine to treat pseudofolliculitis barbae, would also preferably contain, but not be limited to, the following: purified, de-ionized or distilled water; an agent to moisturize and stimulate granulation and formation of new tissue as a result of razor bumps cut by shaving, such as aloe vera; an active skin protectant and stimulant of new and healthy tissue growth such as allantoin; a thickening agent such as xanthum gum; a styptic to stop the bleeding of cut bumps such as alum; a humectant emollient and beard softener such as glycerol; a moisturizing agent for retaining the water in the composition such as propylene glycol. In addition to the above, for a creamier aftershave balm, the composition would also preferably contain, but not be limited to, the following: A lubricant and skin softener such as stearic acid; an anesthetic such as procaine HCL; a preservative antibacteria and anti-fungus agent such as propyl paraben; an emulsifying, dispersing agent such as glycerol monostearate; a multisterol extract derived from lanolin that is a superb moisturizer and emollient as well as an emulsifier and stabilizer such as amerchol lot 101–701; an acetylated lanolin for skin conditioning such as Modulan 500; a lubricant such as silicon; a fragrance such as tincture of mint.

A preferred range of the povidone-iodine complex in a composition to treat pseudofolliculitis barbae should be about, but not limited to, the range of 1.0% to 20.0% by weight of the total composition, most preferably about 10.0% by weight of the total composition. The following examples are illustrative of formulations of compositions according to this invention but are not to be considered as limiting the scope of this invention.

Formulation Procedure

EXAMPLE I

1. Place xanthum gum and distilled water in a container and heat to 65° C. Then, dissolve aloe vera powder-200, alum and allantoin in appropriate proportions into the solution and heat to 72° C. Then, add glycerol, propylene glycol and povidone-iodine in the appropriate proportions and heat to 75° C. Mix well for approximately one hour. Cool to about 80° F. to 110° F. and fill in specified containers. For the treatment of pseudofolliculitis barbae, the resultant mixture is applied to the treatment area one to two times daily, particularly after shaving and before going to bed at night.

EXAMPLE II

A 5.0% povidone-iodine formulation mixed to serve as an aftershave gel lotion.

| Ingredients | Weight Percent |
| --- | --- |
| water | 83.93 |
| xanthum gum | 3.00 |
| aloe vera powder -200 | .58 |
| alum | .68 |
| allantoin | .50 |
| glycerol | 5.82 |
| propylene glycol | .49 |
| povidone-iodine | 5.00 |
| Total | 100.00 |

EXAMPLE III

A 10.0% Formulation of a povidone-iodine mixtue to serve as an Aftershave Gel Lotion.

| Ingredients | Weight Percent |
| --- | --- |
| water | 78.93 |
| xanthum gum | 3.00 |
| aloe vera powder -200 | .58 |
| alum | .68 |
| allantoin | .50 |
| glycerol | 5.82 |
| propylene glycol | .49 |
| povidone-iodine | 10.00 |
| Total | 100.00 |

EXAMPLE IV

A 10.0% Povidone-iodine Formulation of a combination Moisturizer-Aftershave Balm.

| Ingredients | Weight Percent |
| --- | --- |
| Oil Phase | |
| stearic acid | 2.28 |
| procaine HCL | .76 |
| propyl paraben | .93 |
| glycerol monostearate | 2.24 |
| amerchol lot 101-701 | 1.53 |
| modulan 500 | 1.02 |
| silicon | 1.19 |
| tincture of mint | 1.70 |
| Water Phase | |
| water | 71.34 |
| xanthum gum | .13 |
| aloe vera powder -200 | .53 |
| povidone-iodine | 10.00 |
| glycerol | 5.09 |
| propylene glycol | .33 |
| allantoin | .34 |
| alum | .59 |
| Total | 100.00 |

Heat oil phase and water phase separately to 75° C. Mix oil phase and water phase separately until both are uniform. Add oil phase to water phase with constant stirring and mix until uniform. Example IV has advantages in that it results in a creamier aftershave balm.

Thus the reader can see that the inventions disclosed herein, and the methodology for the treatment of pseudofolliculitis barbae disclosed above, which comprises topically applying effective amounts of povidone-iodine in combination with a vehicle which facilitates the topical application of the povidone-iodine, can be used by sufferers of this insidious skin disease both for relief from effects of the condition and for prophylactic treatment of the condition.

While my above description contains many specifics, these should not be construed as limitation on the scope of the invention, but rather as exemplifications of preferred embodiments thereof. Other examples are, combining povidone-iodine in various vehicles that result in skin cleansers, scrubs and soaps, moisturizing balms and other skin care lotions to be used by sufferers of pseudofolliculitis barbae. Accordingly, the scope of my inventions should be determined not by the specific embodiments illustrated, but by the appended claims and their legal equivalents.

I claim:

1. In a method for treating the condition of pseudofolliculitis barbae in humans and effecting a prophylactic treatment of said condition; the improved method of first shaving the area to be treated and then applying a topical treatment to the area that has been shaved, with a topically applied, smearable vehicle, consisting esentially of povidone iodine in an effective amount and as an effective ingredient for treating said condition.

* * * * *